United States Patent
Rockseisen

(10) Patent No.: US 7,710,554 B2
(45) Date of Patent: May 4, 2010

(54) APPARATUS FOR MONITORING THE ALIGNMENT OF MARKING LASERS

(75) Inventor: Armin Rockseisen, Scharnebeck (DE)

(73) Assignee: LAP GmbH Laser Applikationen, Luneburg (DE)

( * ) Notice: Subject to any disclaimer, the term of this patent is extended or adjusted under 35 U.S.C. 154(b) by 470 days.

(21) Appl. No.: 11/736,925

(22) Filed: Apr. 18, 2007

(65) Prior Publication Data

US 2007/0291267 A1 Dec. 20, 2007

(30) Foreign Application Priority Data

Jun. 19, 2006 (DE) .................. 10 2006 028 053

(51) Int. Cl.
*G01B 11/26* (2006.01)

(52) U.S. Cl. .................. 356/141.3; 356/141.1; 356/399

(58) Field of Classification Search ...............
356/139.04–139.08, 141.2–141.4, 399, 400; 378/205, 206
See application file for complete search history.

(56) References Cited

U.S. PATENT DOCUMENTS

| | | | | |
|---|---|---|---|---|
| 3,816,000 A | * | 6/1974 | Fiedler | 356/141.3 |
| 4,889,425 A | * | 12/1989 | Edwards et al. | 356/141.3 |
| 5,142,559 A | | 8/1992 | Wielopolski et al. | |
| 6,023,337 A | * | 2/2000 | Schiff | 356/400 |
| 6,041,249 A | | 3/2000 | Regn | |
| 6,099,522 A | | 8/2000 | Knopp et al. | |
| 2005/0174582 A1 | | 8/2005 | Carr et al. | |

FOREIGN PATENT DOCUMENTS

| | | |
|---|---|---|
| DE | 44 18 216 A1 | 11/1995 |
| EP | 1 211 480 A2 | 10/2001 |
| FR | 94 07672 A1 | 12/1995 |
| GB | 1 0 54 142 A | 2/1981 |
| GB | 2 054 142 A | 2/1981 |
| GB | 2 331 360 A1 | 5/1999 |
| WO | 2006017013 A2 | 2/2006 |
| WO | 2006055770 A2 | 5/2006 |
| WO | 2007124902 A2 | 4/2007 |

* cited by examiner

*Primary Examiner*—L. G Lauchman
(74) *Attorney, Agent, or Firm*—Vidas, Arrett & Steinkraus, P.A.

(57) ABSTRACT

Apparatus for monitoring the alignment of marking lasers in a room for diagnosis and/or treatment in the radiation therapy, characterized by a housing, which is provided with holding means for the installation in the room and which has the following a linearly extending photosensor and an analyzing unit, which compares the position of the light generated by the laser on the photosensor with a reference position, and generates a corresponding signal upon a deviation of the measured position from the reference position.

5 Claims, 2 Drawing Sheets

APPARATUS FOR MONITORING THE ALIGNMENT OF MARKING LASERS

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The present invention is related to an apparatus for monitoring the alignment of marking lasers in rooms for diagnosis and/or treatment in the radiation therapy.

In the radiation therapy, different diagnostic imaging methods are used, which give information about a possible tumour disease as well as about size, shape and position of the tumour. In order to successfully relocate the position of the tumour on a therapeutic device at a later time of irradiation, it is necessary to transmit the spatial information of the diagnostic data to the therapeutic device. For the transmission of the data, it is a conventional method to indicate the isocentre, established in the diagnostic imaging and the subsequent irradiation planning and being the centre of the tumour at the same time, through the projection of laser lines and to mark it on the body of the patient. With the aid of these markings on the patient's body, the patient can be realigned anew at a later time. For example, when the marking has taken place in a diagnostic imaging process, the patient can be aligned anew in the therapy room with respect to fixedly installed lasers, which are aligned to the isocentre of the therapeutic machine and are fine-adjusted. In order to ensure high quality in the alignment, it is necessary to check the alignment, the fine alignment of the lasers in particular.

BRIEF SUMMARY OF THE INVENTION

The present invention is based on the objective to provide an apparatus which makes it possible to check the correct alignment of the marking lasers with simple means, and to indicate possible deviations at an early time.

The apparatus according to the invention serves for monitoring the alignment of marking lasers in rooms for diagnosis and/or treatment in the radiation therapy. The monitoring apparatus is characterized by a housing, which is provided with holding means for the installation in the room and which has a photosensor as well as an analyzing unit. The photosensor is light-sensitive and indicates the position in which light impinges on the photosensor.

The analyzing unit measures the position of the light generated by the laser and compares the same with a predetermined reference position. From the deviation from the reference position, and preferably when a maximum permitted deviation from the reference position is exceeded, the analyzing unit generates a corresponding warning signal, which indicates the missing adjustment. By using photosensors in the monitoring device, the apparatus according to the present invention makes it possible to check the correctness of the adjustment of the marking lasers very accurately.

In a particularly preferred embodiment, the analyzing unit forms a spatial mean value of a spatially distributed signal. In particular, the use of a linearly shaped sensor provides the advantage that even laser lines which are broadened due to the beam divergence can be analyzed in their beam position in a reliable way, which is significantly superior to a purely optical visual check, for instance.

In a preferred embodiment, the analyzing unit is further connected to a central data processing unit via an interface. The data processing unit brings together the signals of the individual analyzing units. Thus, for instance, the position of the laser can not only be checked but also be recorded before starting the operation, in order to reconstruct the alignment thereof later.

In a preferred embodiment, the analyzing unit generates signals for an adjustment device for the alignment of the lasers. Thus, a control signal in order to align the lasers automatically can be generated in addition to the signal which indicates the deviation of the lasers from the reference position. Thus, the fine adjustment of the lasers can be re-adjusted in regular time distances.

BRIEF DESCRIPTION OF THE SEVERAL VIEWS OF THE DRAWINGS

The present invention will now be explained in more detail by means of a realization example.

DETAILED DESCRIPTION OF THE INVENTION

Figure 1:
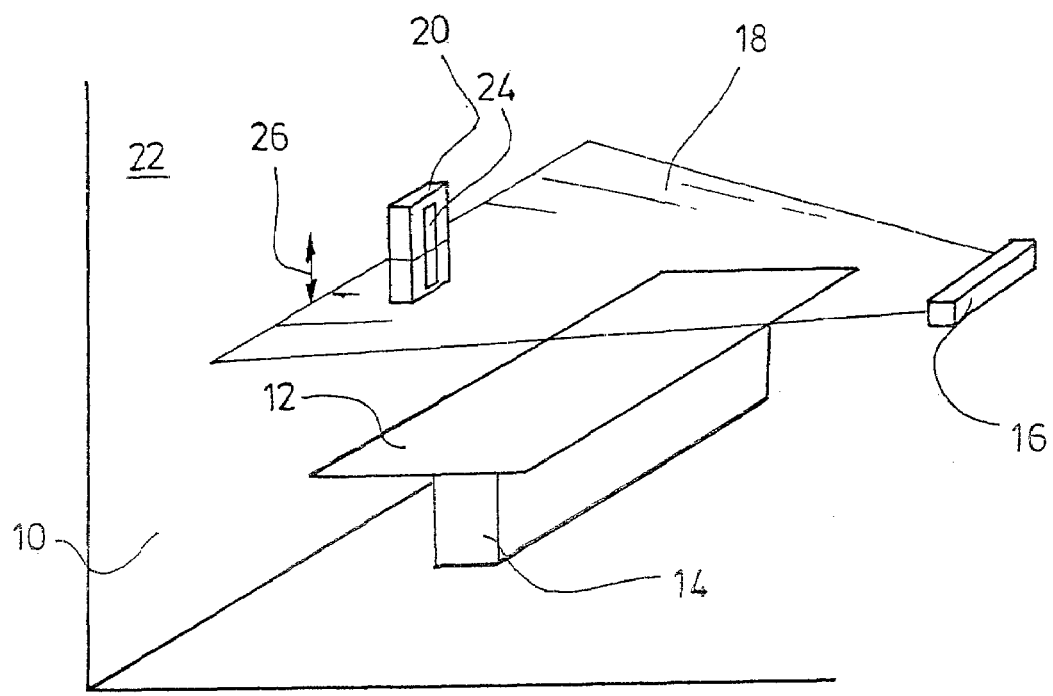
FIG. 1 shows in a schematic view a monitoring apparatus, installed in a room.

While this invention may be embodied in many different forms, there are described in detail herein a specific preferred embodiment of the invention. This description is an exemplification of the principles of the invention and is not intended to limit the invention to the particular embodiment illustrated FIG. 1 shows in a schematic view a room 10 for a therapeutic machine. In the room, a patient support 12 is provided, which can be moved into a desired position with respect to the therapeutic machine (not shown) with the aid of an adjustment unit, disposed in the table foot 14. A patient laying on the support is irradiated by a laterally arranged laser. The laser creates a light plane 18, which runs approximately parallel to the surface of the support 12 in the shown example. The further line lasers are not shown in FIG. 1, which are used for aligning the patient. Usually, a pair of line lasers is arranged laterally on the height level of the patient laying on the support 12, the light planes of which run approximately parallel to the surface of the support 12. Further, a line laser is provided for a sagittal line along the longitudinal axis of the patient. In order to align the patient as accurately as possible, a transversely standing light plane is additionally directed to the patient.

Figure 2:
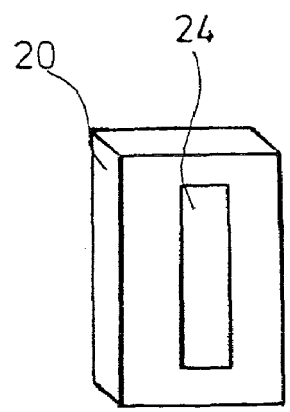
FIG. 2 shows the housing of a monitoring apparatus in a perspective view.

In order to check the fine adjustment of the laser 16, a monitoring device 20 is provided according to the present invention, which is mounted in a predetermined position on the wall 22 in the treatment room. The monitoring device 20 has a line sensor 24 (compare FIG. 2). The line sensor 24 is disposed transversely to the light plane 18 in the installed position. Any deadjustment of the laser 16 along the direction 26 is sensed by the line sensor 24 and can be analyzed here.

Figure 3:
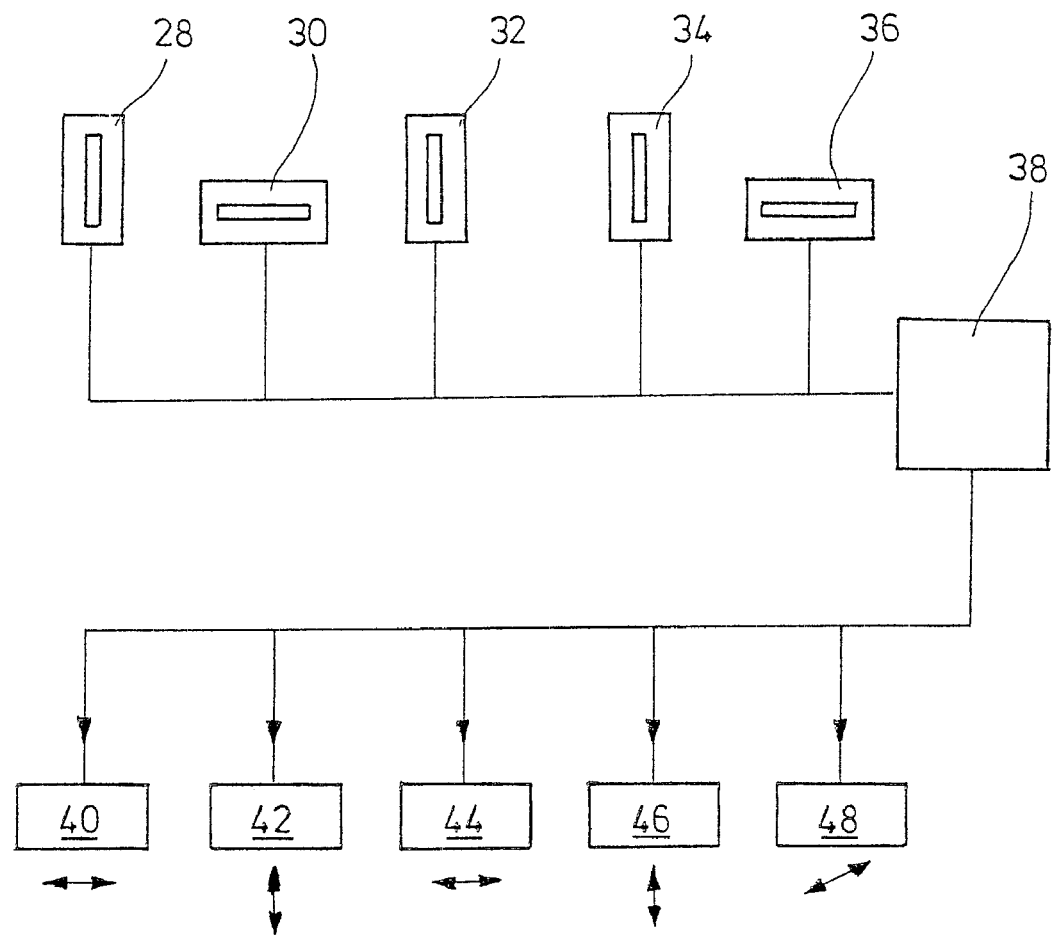
FIG. 3 shows the substantial components with respect to the monitoring and the fine adjustment of the marking lasers, in a block diagram.

FIG. 3 shows a schematic view of an installed monitoring equipment of the alignment of the marking lasers. In the shown example, five monitoring devices 28 to 36 are provided. Each of the monitoring devices detects the position in which the laser impinges on the monitoring device. Besides to the spatial analysis of the measurement results with respect to if the laser signals meet the monitoring device in the predetermined reference position, the position signals are routed to a central computer 38, which analyses the position signals and generates corresponding control signals for an adjustment drive of the lasers. In the realization example shown in FIG. 3, each laser 40 to 48 can be moved forward and back in one direction, respectively. In principle, the control of the adjustment drives could take place also directly by each one of the monitoring devices. Bringing together the position data first in a central computer 38 has the advantage that adjustment operations can be journalized centrally, and thus, systematic errors can be detected more easily, for instance.

The holding means for the monitoring device have also the advantage that the same can be realized as detachable holding means, so that the device according to the present invention is not irradiated itself during the irradiation, for example.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. Apparatus for monitoring the alignment of at least one marking lasers (16) in a room for diagnosis and/or treatment in the radiation therapy, characterized by a housing, which is provided with holding means for the installation in the room and which is provided with at least one linearly extending photosensor (24) and an analyzing unit, which compares the position of the light generated by the at least one marking laser on the at least one photosensor with a reference position, and generates a corresponding signal upon a deviation of the measured position from the reference position.

2. Apparatus according to claim 1, characterized in that the analyzing unit forms the spatial mean value of the sensor signal when the signal is spatially distributed on the sensor.

3. Apparatus according to claim 1, characterized in that the analyzing unit is connected to a central data processing unit (38) via an interface.

4. Apparatus according to claim 3, characterized in that the data processing unit (38) memorises the position of the light on the photosensor.

5. Apparatus according to claim 1, characterized in that the analyzing unit generates signals for an adjustment device for the alignment of the at least one marking laser.

* * * * *